United States Patent
Geistert et al.

(10) Patent No.: US 7,787,963 B2
(45) Date of Patent: Aug. 31, 2010

(54) DEVICE FOR INSERTION OF ELECTRODE LINES OR OTHER MEDICAL INSTRUMENTS INTO A BODY

(75) Inventors: Wolfgang Geistert, Rheinfelden (DE); Erhard Flach, Berlin (DE)

(73) Assignee: BIOTRONIK CRM Patent AG (CH)

( * ) Notice: Subject to any disclaimer, the term of this patent is extended or adjusted under 35 U.S.C. 154(b) by 621 days.

(21) Appl. No.: 11/753,320

(22) Filed: May 24, 2007

(65) Prior Publication Data
US 2008/0015517 A1 Jan. 17, 2008

(30) Foreign Application Priority Data
Jul. 13, 2006 (DE) .................. 10 2006 032 583

(51) Int. Cl.
*A61N 1/05* (2006.01)
(52) U.S. Cl. .................. 607/122; 607/116; 600/374; 600/585
(58) Field of Classification Search .................. None
See application file for complete search history.

(56) References Cited

U.S. PATENT DOCUMENTS

| | | | | |
|---|---|---|---|---|
| 4,198,991 | A | * | 4/1980 | Harris .................. 607/122 |
| 5,029,585 | A | | 7/1991 | Lieber et al. |
| 5,119,832 | A | * | 6/1992 | Xavier .................. 607/117 |
| 5,409,652 | A | | 4/1995 | Carter |
| 5,681,514 | A | * | 10/1997 | Woody .................. 264/104 |
| 6,159,189 | A | | 12/2000 | Finnemore et al. |
| 6,251,092 | B1 | | 6/2001 | Qin et al. |
| 6,450,972 | B1 | | 9/2002 | Knoll |
| 6,475,214 | B1 | | 11/2002 | Moaddeb |
| 6,595,991 | B2 | | 7/2003 | Tollner et al. |
| 6,892,087 | B2 | | 5/2005 | Osypka |
| 7,231,259 | B2 | * | 6/2007 | Jenney et al. .................. 607/116 |
| 2003/0083560 | A1 | | 5/2003 | Osypka |

(Continued)

FOREIGN PATENT DOCUMENTS

DE  10008918 A1  8/2001

(Continued)

OTHER PUBLICATIONS

European Search Report, Patent No. 07011929.2-2310, Nov. 7, 2005.

*Primary Examiner*—Kennedy J Schaetzle
(74) *Attorney, Agent, or Firm*—Craig A. Fieschko, Esq.; DeWitt Ross & Stevens S.C.

(57) ABSTRACT

An insertion device (10), by which a medical instrument or an electrode line or a guide wire or a medical therapeutic agent may be inserted into a body cavity, comprises a lumen section (11) manufactured from a flexible plastic material, having a longitudinal axis, a proximal end and a distal end, and a distal end area enclosing the distal end, at least one electrically conductive means (20) in the distal end area to sense physiological signals or stimulate the surrounding body tissue suitably, as well as at least one conductor, which extends from the proximal end to the distal end and is capable of conducting physiological signals to the proximal end and/or stimulation pulses to the distal end. The at least one electrically conductive means is produced from a flexible, not exclusively metallic, electrically conductive substrate.

17 Claims, 1 Drawing Sheet

U.S. PATENT DOCUMENTS

2006/0030833 A1 2/2006 Harris et al.

FOREIGN PATENT DOCUMENTS

| EP | 0 582 766 A1 | 2/1994 |
| EP | 0 898 481 B1 | 11/1997 |
| EP | 0 986 325 B1 | 12/1998 |
| EP | 1 151 726 A1 | 11/2001 |
| GB | 2 268 071 A | 1/1994 |
| WO | WO 99/33509 A | 7/1999 |
| WO | WO 99/33509 A1 | 7/1999 |
| WO | WO 02/058785 A1 | 8/2002 |
| WO | WO 03/034932 A1 | 5/2003 |
| WO | WO 2004/050156 A1 | 6/2004 |

* cited by examiner

DEVICE FOR INSERTION OF ELECTRODE LINES OR OTHER MEDICAL INSTRUMENTS INTO A BODY

FIELD OF THE INVENTION

The present invention relates to an insertion device for inserting a medical instrument, an electrode line, a guide wire, or a medical therapeutic agent into the body cavity of a human or animal body.

BACKGROUND OF THE INVENTION

The foregoing insertion devices are known, for example, as insertion catheters and are used for placing a cardiac electrode line or a guide wire in the interior of the heart, in a coronary artery of the heart—such as the coronary sinus—or in a blood vessel connected adjoining the heart—such as the vena cava. Cardiac electrode lines are lines which produce an electrical contact between an electrically active implant such as a cardiac pacemaker or an implantable cardioverter/defibrillator (ICD) and an electrode head electrically connected to the heart, to stimulate the heart or record physiological measured values. Special embodiments of such electrodes, so-called "over the wire" electrodes, may be placed with the aid of a guide wire.

An insertion device of the type cited has a distal end, which faces toward the heart, and a proximal end, which is located outside the body and which is operated by the operator. A lumen section manufactured from a flexible plastic is located between the two ends, through whose lumen and the openings at the proximal and distal ends the cardiac electrode line or the guide wire is inserted. This lumen section has a diameter tailored to the thickness of the electrode line and/or the guide wire. After the insertion of the insertion device—if the distal end of the insertion device has been maneuvered to the desired point—an electrode line and/or a guide wire is inserted from the proximal end and then anchored on or in the heart by suitable fasteners.

A known problem of such insertion devices is that it is not possible to remove them simply by pulling them out, because the plug on the proximal end of the electrode line has a larger diameter than the lumen section of an insertion catheter due to standardized dimensions. Removal by shifting the insertion device in the proximal direction is thus not possible. This problem is solved according to the prior art in that the cited insertion devices may be slit or torn open from the proximal end to the distal end. It is thus made possible to remove the insertion device easily after placement of the electrode line. These insertion devices are often designed as directionally controllable, so that the placement is simplified. Such controllable and/or slittable insertion devices are described in EP 0 898 481, U.S. Pat. No. 6,159,198, and WO 99/33509.

In daily practice using such insertion devices, it has proven to be desirable to measure electrical signals such as electrical potentials or physiological signals during the insertion process of cardiac electrodes, to thus obtain a first impression of the physiological status of the fastening/stimulation location. Sometimes, it is also necessary to deliver stimulation pulses to thus find the optimum fastening/stimulation location of the electrode. This problem has been solved in insertion devices from the prior art in that at least one electrode is provided in the distal area, which may execute the cited functions. The measurement or stimulation pulses are generated by external stimulation threshold analyzers, for example. These units may record and/or process and analyze measured values from the heart. Such units are also used for delivering stimulation pulses and even for delivering defibrillation shocks in case of emergency.

WO 02/058785 discloses an insertion device having at least one electrode in the lumen section. The at least one electrode is manufactured from a metallic conductive material. A slittable or tearable insertion device is disclosed in U.S. Pat. No. 6,892,087, in which an electrode is situated on a dilator and the counter electrode is situated on the distal end of the insertion device. The at least one electrode is manufactured from metal, such as platinum or iridium or alloys thereof.

These two cited insertion devices from the prior art have the disadvantage, however, that the slitting and/or tearing open is possible not at all or only with great difficulty. The electrodes must additionally be thin-walled to keep the ratio of external diameter to lumen diameter of the lumen section small. Such an open, thin-walled metal electrode is very sharp-edged and may thus cause injuries during use.

SUMMARY OF THE INVENTION

The present invention is based on the object of avoiding the above-mentioned disadvantages of the prior art and providing an insertion device wherein, during the use at the fastening/stimulation location of an electrode line, electrical and physiological body signals may be measured and/or the body tissue may be stimulated.

The device according to the present invention contains an insertion device, through which a medical instrument or an electrode line or a guide wire or a medical therapeutic agent may be inserted into a body cavity of a human or animal body. It comprises a lumen section manufactured from a flexible plastic material having a longitudinal axis, a proximal end and a distal end, and a distal end area enclosing the distal end, at least one electrically conductive means in the distal end area to sense physiological signals or stimulate the surrounding body tissue suitably, as well as at least one conductor, which extends from the proximal end to the distal end and is capable of conducting physiological signals to the proximal end and/or stimulation pulses to the distal end. The at least one electrically conductive means is produced from a flexible, not exclusively metallic electrically conductive substrate, to prevent trauma upon insertion of the insertion device into the human or animal body.

A flexible, not exclusively metallic electrically conductive means may be a conductive plastic, conductive adhesive, or a flexible thermal bridge known from circuitry technology. For example, it comprises a non-degradable biocompatible polymer such as polyurethane or Pebax, in which extremely fine particles of a conductive material are embedded. The embedded conductive material may be a metal powder, for example, any electrically conductive metal, preferably gold, silver, or platinum powder, being suitable as the metal powder. Powders made of metal alloys, such as platinum/iridium, are also suitable. Instead of a metal or metal alloy powder, powders made of carbon, preferably in graphite form, may also be used. The following conductive plastics and adhesives have been shown to be especially suitable: Staystik, Elecolit.

The particles are embedded in the substrate in such a way that they are partially in mutual contact and thus form a current path. The specific resistance of such as substrate is determined by the concentration of the conductive particles in the polymer matrix, by the specific resistance of the particle material itself, and by the quality and type of the embedding, for example.

The specific resistances of such conductive plastics move in the range from 0.05 mΩcm to 100 Ωcm.

The advantage achieved by the present invention is that insertion devices having an electrically conductive means made of a flexible, not exclusively metallic, electrically conductive substrate cause fewer injuries in use in the human or animal body because of their lower hardness. They are also easy to slit or tear open.

The electrically conductive means made of a flexible, not exclusively metallic electrically conductive substrate may be produced premolded and then glued, welded, or melted onto the distal end of the insertion device. Alternatively, the electrically conductive means may be attached to the flexible lumen section by applying a conductive plastic (e.g., a conductive adhesive) in solution to the distal end of the lumen section of the insertion device. After the solvent evaporates, the electrically conductive means remains. In this way, it is possible to produce insertion devices having an electrically conductive means made of a flexible, electrically-conductive substrate which is not exclusively metallic in nearly any arbitrary size and shape.

The electrically conductive means is advantageously placed at the distal end of the insertion device and the active area of the conductive means is oriented in the direction of the distal end. Such an insertion device is moved orthogonally to the tissue and pressed against the tissue using the distal end. Therefore, the largest possible contact area to the tissue results with electrically conductive means oriented exclusively in the distal direction, which has an advantageous effect on the measurement of body signals and the stimulation of the body tissue.

The electrically conductive conductor, which connects the electrically conductive means to the proximal end of the insertion device, is a single wire connected to the wall of the lumen section or embedded in this wall. Preferably, the connection may also be produced via an insulated web made of conductive plastic embedded in the lumen wall. Especially preferably, the stiffening element or braid—comprising an electrically conductive material—of the insertion device provided in the lumen wall may also be used as a supply line.

In a further preferred way, the wall of the lumen section has at least three layers, which extend along the longitudinal axis of the lumen section from the distal to the proximal end. One of the layers is made of electrically conductive plastic and forms the electrically conductive conductor(s). The layer made of electrically conductive plastic is enclosed on its inner and outer surfaces by a dielectric layer to produce insulation.

At least one of the dielectric layers is preferably removed in the distal end area, to thus produce a simple connection to the electrically conductive means, or this area itself forms the electrically conductive means situated radially around the longitudinal axis in a partial circle.

Of course, further possible applications of such an insertion device result, for example, in the placement of electrode lines outside the heart, such as lines for nerve stimulation, lines for stimulation of specific brain regions, or other intracorporal application areas of electrical treatment signals, which are emitted by an electrically active implant. The use of such an insertion catheter is performed similarly as in the application thereof on the heart.

Further advantageous embodiments of the present invention are described below.

DETAILED DESCRIPTION OF PREFERRED VERSIONS OF THE INVENTION

Figure 1A:
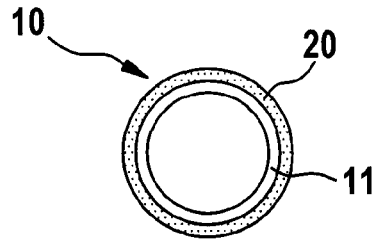
FIGS. 1a and 1b: show the distal end of the insertion device according to the present invention in a preferred embodiment in a top view from the distal end and in a side view.
Figure 1B:
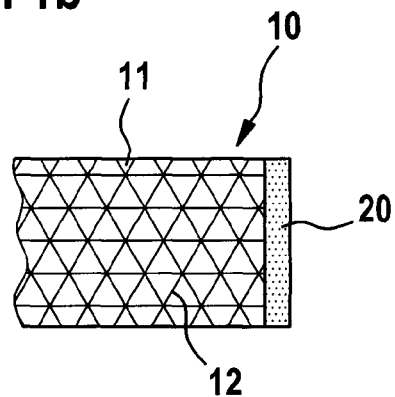

FIGS. 1a and 1b show a schematic illustration of the distal end of a catheter 10, in which an electrode 20 made of conductive plastic is attached to the distal end of the lumen section 11.

The electrode 20 is connected to the metallic reinforcement braid 12, which is embedded in the lumen section 11. The reinforcement braid 12 is used, in addition to increasing the rigidity of the lumen section 11, as the electrical connection of the electrode 20 to the proximal area of the insertion catheter (not shown), on which a plug connector of arbitrary, known construction is situated. In the area in which the electrode 20 is seated, the external part of the lumen section is removed by abrasion, for example, so that the reinforcement braid 12 is exposed. The electrode 20 is attached to the distal end of the catheter in such a way that there is an electrical connection between braid and electrode. The electrical connection may be produced by melting a prefinished, annular electrode or by "painting" or printing on the electrode made of viscous, conductive plastic (e.g., conductive adhesive). Alternatively, the electrode may also be incorporated directly into the lumen section during its production.

Figure 2A:
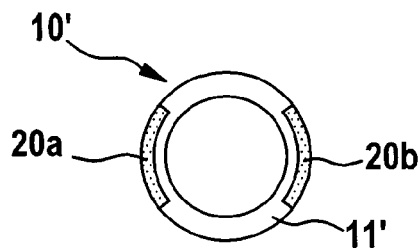
FIGS. 2a and 2b: show the distal end of the insertion device according to the present invention in a further preferred embodiment in a top view from the distal end and in a side view.
Figure 2B:
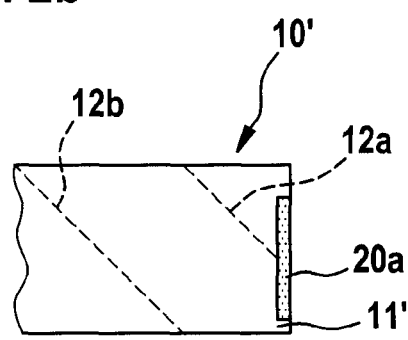

FIG. 2a and FIG. 2b show the schematic illustration of a further preferred embodiment of the distal end of a catheter 10', in which two electrodes 20a, 20b made of conductive plastic are attached in a partial circle on the distal end of the lumen section 11'.

Each of the electrodes 20a or 20b is connected to one wire 12a or 12b on the distal end of the catheter 10'. Both wires 12a, 12b are embedded insulated in the material of the lumen section 11'. The wires 12a, 12b are used as the electrical connection of the electrodes 20a, 20b to the proximal area of the insertion catheter (not shown), on which an at least 2-pole plug connector is situated. The wires 12a, 12b may be embedded in a spiral in the lumen section 11'.

Figure 3A:
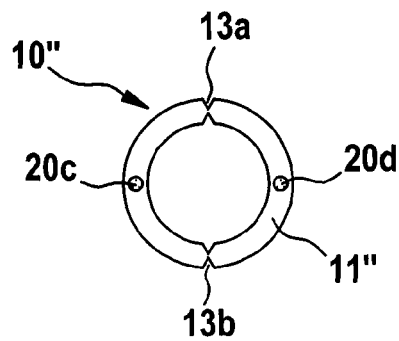
FIGS. 3a and 3b: show the distal end of the insertion device according to the present invention in another preferred embodiment in a top view from the distal end and in a side view
Figure 3B:
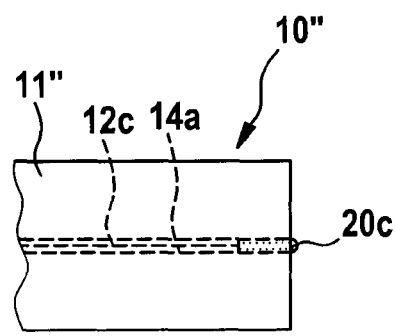

FIG. 3a and FIG. 3b show a schematic illustration of another preferred embodiment of the distal end of a catheter 10", in which two electrodes 20c and 20d made of conductive plastic are attached to the distal end of the lumen section 11". Two intended breakpoints 13a and 13b are also shown in this figure, which are provided along the longitudinal axis of the catheter 10" in the lumen section from the proximal end to the distal end of the catheter 10" and allow the lumen section 11" to be torn open easily. The intended breakpoints 13a and 13b are designed in such a way that targeted material changes or material diminutions of the lumen section 11" result in tearing of the wall of the lumen section 11" at these predefined intended breakpoints 13a and 13b in the event of a shear load along the longitudinal axis of the lumen section. This material change may be performed by perforation, for example. Further embodiments, such as tear wires along the intended breakpoints 13a and 13b, may be provided.

The lumen section 11" of the catheter 10" has two lumens, one shown at 14a, which extend along the longitudinal axis of the catheter 10" from the distal to the proximal end, in each of which a supply line wire is situated, one being shown at 12c. Such a lumen 14a having a supply line wire 12c is indicated in FIG. 3b. The supply line wire 12c ends shortly before or approximately at the distal end of the catheter 10" and is embedded there by an electrical contact in the electrode 20c. The electrode 20c projects slightly into the lumen 14a on one side to produce the electrical contact to the supply line wire 12c and projects beyond the distal end of the catheter 10" on the other side. In this way, the electrical contact between electrode 20c or 20d and the surrounding tissue is produced during application of the catheter 10".

Figure 4A:
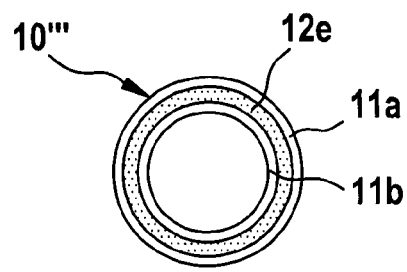
FIGS. 4a and 4b: show the distal end of the insertion device according to the present invention in another especially preferred embodiment in a top view from the distal end and in a side view
Figure 4B:
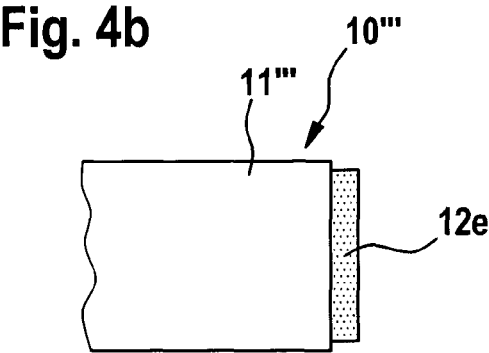

FIG. 4a and FIG. 4b show a schematic illustration of another especially preferred embodiment of the distal end of a catheter 10'", in which the wall of the flexible lumen section 11 is constructed from three layers, which extend along the longitudinal axis of the lumen section from the proximal end to the distal end. Two dielectric layers 11a and 11b enclose an electrically conductive layer 12e, which is used as an electrical connection between an electrically conductive means of the previously cited type and a plug connector on the proximal end (not shown). The electrically conductive layer preferably comprises electrically conductive plastic.

The electrically conductive layer 12e may be exposed on the distal end. This exposed end is produced by removing the dielectric layers 11a and 11b over a section on the distal end. This removal may be performed by abrasion, etching, or other suitable methods, for example. Preferably, only the outer of the two dielectric layers 11a may also be removed and an electrically conductive means—as in FIG. 1a, 1b, 2a, 2b, 3a, or 3b, for example—may be electrically connected. The electrical connection may be performed by melting on a prefinished, annular electrode or by "painting" or printing on an electrode made of viscous, conductive plastic (e.g., conductive adhesive).

What is claimed is:

1. An insertion device by which a medical instrument or an electrode line or a guide wire or a medical therapeutic agent may be inserted into a body cavity of a human or animal body, comprising:
   a. a lumen section formed of a flexible plastic material, having a longitudinal axis, a proximal end and a distal end, and a distal end area adjacent the distal end;
   b. at least one electrically conductive terminal in the distal end area to sense physiological signals or to stimulate the surrounding body tissue, the terminal:
      (1) being formed from a flexible, not exclusively metallic electrically conductive substrate,
      (2) being exposed both:
         i. at the distal end, and
         ii. along only a portion of an outer circumference of the distal end area; and
   c. at least one electrically conductive conductor extending from the proximal end to the distal end along a helical path, the conductor being capable of conducting physiological signals to the proximal end and/or simulation pulses to the distal end.

2. The insertion device of claim 1 wherein there are two or more electrically conductive terminals spaced from each other, each extending in a circumferential direction at least partially around the lumen section.

3. The insertion device of claim 1 wherein the electrically conductive terminal and/or the at least one electrically conductive conductor comprises electrically conductive plastic.

4. The insertion device of claim 3 wherein the electrically conductive plastic is a polymer filled with metal or carbon particles.

5. The insertion device of claim 1 wherein each conductor:
   a. extends to a respective electrically conductive terminal, and
   b. is spaced from any conductor leading to any other electrically conductive terminal.

6. The insertion device of claim 1 wherein each terminal is defined by a portion of an annular ring.

7. An insertion device for insertion of matter into a body cavity, the device including:
   a. an elongated flexible lumen section having:
      (1) a proximal end and a distal end,
      (2) an outer surface extending from the distal end, wherein at least a substantial portion of the outer surface is not electrically conductive;
      (3) an internal channel extending along the length of the lumen section and opening onto the distal end;
   b. at least one electrically conductive terminal at or adjacent to the distal end, the terminal being exposed along the outer surface of the lumen section;
   c. electrically conductive conductors extending from the proximal end to the terminal, the conductors:
      (1) being helically wound about the longitudinal axis of the lumen section,
      (2) defining a braid extending to the terminal, wherein the braid is exposed along the outer circumference of the lumen for a length prior to the terminal.

8. The insertion device of claim 7 wherein the terminal defines at least a portion of an annular ring.

9. The insertion device of claim 7 wherein the terminal is formed of at least one of:
   a. carbon particles, and
   b. metallic particles,
   embedded in a polymeric matrix.

10. The insertion device of claim 9 wherein the conductor is formed of at least one of:
    a. carbon particles, and
    b. metallic particles,
    embedded in a polymeric matrix.

11. The insertion device of claim 7 wherein the terminal is exposed both:
    a. at the distal end, and
    b. along a portion of an outer circumference of the distal end.

12. The insertion device of claim 11 wherein the terminal is defined by an annular ring.

13. The insertion device of claim 12 wherein the lumen section:
    a. is not electrically conductive, and
    b. is situated within the entirety of the circumference of the annular ring at the distal end.

14. An insertion device for insertion of matter into a body cavity, the device including:
    a. an elongated lumen section extending from a proximal end to a distal end, the lumen section having a nonconductive outer surface;
    b. one or more conductive terminals at or adjacent to the distal end, the terminals being:

(1) exposed along the outer surface of the lumen section, and
(2) formed of conductive material embedded within a polymeric matrix;
c. one or more conductors extending within the lumen section from the proximal end to the terminals, wherein each conductor:
(1) is embedded within the lumen section so that it is not conductively exposed along the outer surface of the lumen section, and
(2) extends helically about the lumen section to a respective terminal, with the conductors of each terminal being spaced about the circumference of the lumen from the conductors of the other terminals.

15. The insertion device of claim 14, wherein each terminal is exposed along the distal end.

16. The insertion device of claim 14, wherein the lumen:
a. is nonconducting,
b. includes an internal channel opening onto the distal end, and
b. spaces each terminal from the internal channel.

17. The insertion device of claim 16 wherein each terminal is defined by a portion of an annular ring.

* * * * *